United States Patent [19]
Yang et al.

[11] Patent Number: 5,892,087
[45] Date of Patent: Apr. 6, 1999

[54] PROCESS FOR DECOMPOSING SILOXANE BOND-CONTAINING COMPOUND

[75] Inventors: Jae-Kun Yang, Joogong Apt. #606-1405,Gaepo-dong, Kangnam-ku, Seoul; Jeong-Ryeon Han, Samwoo Villa #501, 48-30, Jangchoong-dong 1-ga, Joong-ku, Seoul; Joung-Bum Shin; Jae-Jin Hong, both of Seoul, all of Rep. of Korea

[73] Assignees: Jae-Kun Yang; Jeong-Ryeon Han, both of Seoul, Rep. of Korea

[21] Appl. No.: 10,933

[22] Filed: Jan. 22, 1998

[30] Foreign Application Priority Data

Jan. 22, 1997 [KR] Rep. of Korea ............... 1997-1764

[51] Int. Cl.⁶ .................................................. C07F 7/08
[52] U.S. Cl. ............................................................ 556/467
[58] Field of Search ............................................... 556/467

[56] References Cited

U.S. PATENT DOCUMENTS

| | | | |
|---|---|---|---|
| 2,698,861 | 1/1955 | Shorr | 556/467 |
| 2,826,599 | 3/1958 | Meals | 556/467 |
| 2,837,552 | 6/1958 | George et al. | 556/467 |
| 4,310,680 | 1/1982 | Kotzsch et al. | 556/467 |
| 4,417,067 | 11/1983 | Kotzsch et al. | 556/467 |
| 5,504,235 | 4/1996 | Hirose et al. | 556/467 |
| 5,534,608 | 7/1996 | Thompson et al. | 556/467 X |

*Primary Examiner*—Paul F. Shaver
*Attorney, Agent, or Firm*—Oblon, Spivak, McClelland, Maier & Neustadt, P.C.

[57] ABSTRACT

The present invention relates to a novel process for decomposing siloxane bond-containing compound by an alkali decomposer characterized in that one or more selected from a group consisting of secondary and tertiary aliphatic alcohols are used as a decomposition facilitator, and if desired, the decomposition product is further sonicated and treated with a triorganylhalosilane.

17 Claims, 11 Drawing Sheets

PROCESS FOR DECOMPOSING SILOXANE BOND-CONTAINING COMPOUND

TECHNICAL FIELD

The present invention relates to a novel process for decomposing siloxane bond-containing compound by an alkali decomposer characterized in that one or more selected from a group consisting of secondary and tertiary aliphatic alcohols are used as a decomposition facilitator, and if desired, the decomposition product is further sonicated and treated with a terminator.

BACKGROUND ART

Silixane bond-containing compounds include polyorganosiloxanes, such as for example, silicone resin, silicone rubber, etc. A good deal of the siloxane bond-containing compound is conventionally discarded in the form of waste matters due to the combination failure during processing step, scraps formed in finishing step, or useless materials from a variety of industrial areas. Such a discarded silicone resin or silicone rubber can hardly be re-used because it's reclamation is almost impossible. Furthermore, since there have not developed as yet any effective cleavage methods for the discarded silicone resin and rubber, they are usually left untreated. Accordingly, processing factories have great difficulties to treat the wastes.

Chemical cleavage methods for siloxane bond-containing compound include decompositions by heat, acid, or alkali. Among those methods, a process for producing alkali metal trimethylsilanolate by heating hexamethyldisiloxane in the presence of an alkali metal hydroxide or alkoxide, as depicted in the following reaction scheme 1, can be exemplified as a related one to the process according to the present invention (see, J. F. Hyde et al, *J Am. chem. Soc.*, 75, 5615, 1953; W. S. Tatlock and E. G. Rochow, *J. Am. Chem. Soc.*, 72, 528, 1950).

Reaction Scheme 1

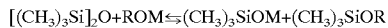

[(CH$_3$)$_3$Si]$_2$O+ROM⇌(CH$_3$)$_3$SiOM+(CH$_3$)$_3$SiOR in which

R represents hydrogen atom or alkyl, and

M represents Na, K or Li.

In addition, as depicted in the following reaction scheme 2, a process wherein potassium or sodium siloxanediolate is produced through the cleavage of cyclodiorganylsiloxane or straight polydiorganylsiloxane having a high molecular weight by potassium hydroxide or sodium hydroxide in the presence of a primary alcohol such as methanol, ethanol, etc. is disclosed in T. Takiguchi and M. Skural, Kogyo Kagaku Zassi, 63, 1476, 1960; W. Noll, Chemie und Technologie der Silicone, Verlag Chemie, Weinheim, 1968; A. Stock and C. Somieski, Ber., 52, 595, 1919; J. F. Hyde, J. Am. Chem. Soc., 75, 2166, 1953; and K. A. Andrianov and M. A. Sipyagina, Izv. Akad. Nauk SSSR, Neorg. Mat., 4, 2016, 1968.

Reaction Scheme 2

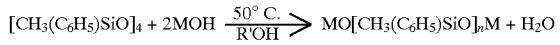

[CH$_3$(C$_6$H$_5$)SiO]$_4$ + 2MOH $\xrightarrow[\text{R'OH}]{50° C.}$ MO[CH$_3$(C$_6$H$_5$)SiO]$_n$M + H$_2$O in which M represents Na or K, and R' represents methyl or ethyl.

In the alkali-decomposition method as mentioned above, however, it is difficult to control the reaction since a primary alcohol such as methanol, ethanol, etc. is used as a decomposition facilitator. Also, according to this method, silica combined as a filler may not efficiently be recovered; the cleavage yield is low; and the molecular weight of the decomposition product is high.

It is described in the above alkali-decomposition method that secondary or tertiary alcohols can be used during the cleavage in addition to primary alcohols. However, since it is also described therein that "Secondary alcohols react with siloxanes in the presence of KOH or ROK more slowly than do primary alcohols, while tertiary alcohols are completely unreactive", the technical concept of the existing alkali-decomposition method is quite different from that of the present invention.

DISCLOSURE OF INVENTION

Under such technical circumstances, the present inventors have extensively studied to develop an efficient decomposition method for siloxane bond-containing compound, such as for example, silicone rubber, silicone resin, silica, etc. which are recently discarded as wastes in a great amount. As a result, we have identified that such a purpose can be effectively achieved if one or more selected from a group consisting of secondary and tertiary aliphatic alcohols are used as a decomposition facilitator, and thus completed the present invention. Further, the present inventors have found during the studies that the decomposition product thus obtained may be sonicated and then treated with a terminator in the presence of a decomposer and decomposition facilitator to prepare a decomposition product having a lower molecular weight or a less particle diameter. Therefore, such an additional process is also included in the scope of the present invention.

Therefore, the present invention provides a process for decomposing siloxane bond-containing compound by an alkali decomposer characterized in that one or more selected from a group consisting of secondary and tertiary aliphatic alcohols are used as a decomposition facilitator.

The present invention also provides a process for decomposing siloxane bond-containing compound characterized in that the siloxane bond-containing compound is decomposed by an alkali decomposer in the presence of one or more selected from a group consisting of secondary and tertiary aliphatic alcohols are used as a decomposition facilitator and then the decomposition product is sonicated and treated with a terminator after the decomposer and the decomposition facilitator are introduced into the reaction system.

The present invention will be specifically explained in the following.

BRIEF DESCRIPTION OF DRAWINGS

For a thorough understanding of the nature and objects of the invention, reference should be made to the following detailed description taken in connection with the accompanying drawing in which.

BEST MODE FOR CARRYING OUT THE INVENTION

Figure 1:
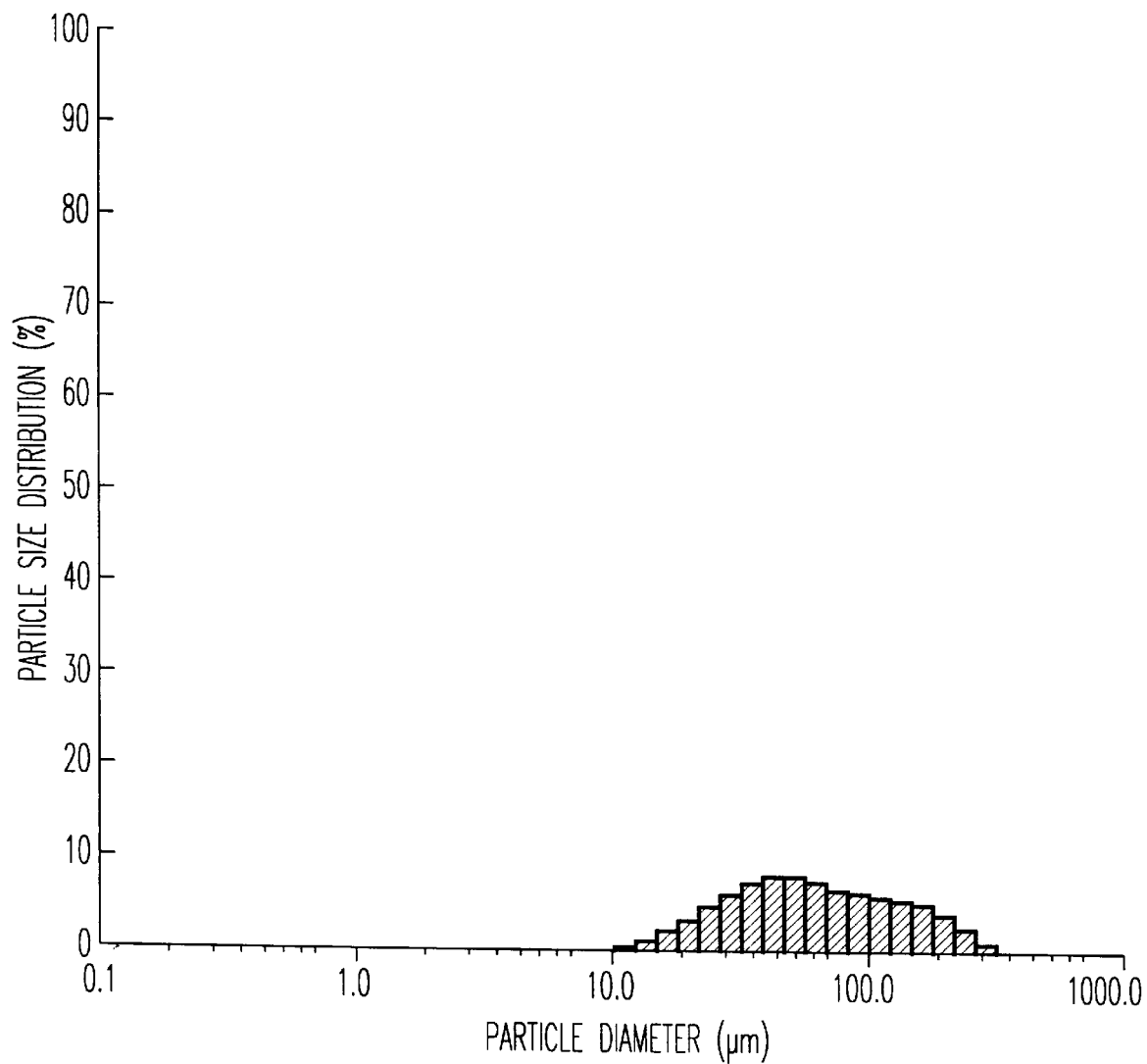
FIG. 1 represents the particle size analysis diagram of the fumed silica used in Reference Example 1.

As mentioned above, it is known that secondary or tertiary alcohols can be added in the decomposition process of siloxane bond by alkali. However, the present inventors have found the astonishing fact that secondary and/or tertiary alcohols can still more effectively facilitate the cleavage of siloxane bond than do primary alcohols, which is a quite different understanding from the earlier one. The present invention is based on such an unexpected discovery.

As the secondary or tertiary alcohol which is used as a decomposition facilitator in the present invention, $C_1$–$C_{10}$ aliphatic alcohols having a boiling point of 130° C. or less, such as for example, isopropanol, 2-butanol, 2-methyl-2-propanol, 2-pentanol, 3-pentanol, 2-methyl-2-butanol, t-amyl alcohol, etc. can be mentioned. In the present invention, a decomposition facilitator having a boiling point of 130° C. or less is used because the decomposition product can be more conveniently recovered. For the other chemicals used in the present invention, it is desirable to use those having a boiling point of 130° C. or less with the same reason. When a mixture of secondary and tertiary aliphatic alcohols is used, the secondary alcohol is conventionally used in an amount of 1 to 10 times by volume with respect to the tertiary alcohol.

If desired, in addition to the use of secondary and/or tertiary aliphatic alcohols, $C_1$–$C_{10}$ primary aliphatic alcohol or $C_6$–$C_{10}$ alkyl, each of which has a boiling point of 130° C. or less, may be used. In the present invention, the primary aliphatic alcohol dilutes the reaction solution which usually has a quite high viscosity into a solution of an appropriate viscosity, whereby helps the reaction to be proceeded without any problem. The alkyl acts as a diluent and also may act as a swelling agent to exert a positive influence upon the reaction.

The primary aliphatic alcohol which can be used in the present invention includes methanol, ethanol, n-propanol, 1-butanol, neopentyl alcohol, etc. It is preferable to use a cheap primary alcohol having a fewer carbon atoms. As the $C_6$–$C_{10}$ alkyl, n-hexane, n-heptane, 2-methyl hexane, 3-methyl hexane, 2,3-dimethyl hexane, 2,4-dimethyl hexane, n-octane or their structural isomers can be mentioned.

When the primary aliphatic alcohol is added, it is preferable to control the ratio of the primary alcohol with respect to the secondary and/or tertiary alcohol to 1:1 to 1:10 by volume. Also, it is good to maintain the total amount of the aliphatic alcohols among the reaction solution constantly whether the primary aliphatic alcohol is used or not. That is, it is usually desirable to control the total amount of the aliphatic alcohols with respect to the material to be decomposed to 30 to 300% by weight when the siloxane bond-containing compound is polyorganosiloxane compound, and it is desirable to control to 300 to 600% by weight when the siloxane bond-containing compound is silica.

The $C_6$–$C_{10}$ alkyl is preferably used in an amount of 1 to 70% by weight with respect to the secondary and/or tertiary aliphatic alcohols.

However, the amounts of each chemicals can be varied with the kind of chemicals, materials to be decomposed, or the reaction conditions, and conventionally the prefered amounts are easily determined by a person skilled in this art within the above mentioned ranges.

As the alkali decomposer used in the process according to the present invention, alkali metal hydroxide or alkoxide, for example, sodium hydroxide, potassium hydroxide, sodium methoxide, potassium methoxide, etc. can be mentioned. It is preferable to use the decomposer in an amount of 5 to 40% by weight with respect to the polyorganosiloxane compound and 20 to 150% by weight to the silica. If the decomposer is used in an amount of less than the aforementioned range the cleavage reaction may not be proceeded smoothly, and if the amount exceeds the range the physico-chemical properties of the resulting silica may be deteriorated due to the alkali metal silicate formed during the cleavage.

When siloxane bond-containing compound is decomposed using the decomposer and decomposition facilitator as explained above, the desired cleavage reaction can be completed by reacting for one hour to 3 days under atmospheric pressure or pressurized at temperatures ranging from −20° C. to 100° C. The reaction pressure, time and temperature can be varied with the kind of materials to be decomposed or the degree of decomposition within the above mentioned ranges. Since the temperature, pressure and time are complementary to each other, temperature and time, for example, may be depended upon the selected pressure. The corelation between temperature, pressure and time determined by experiments can be exemplified as the following Table 1.

TABLE 1

| 1 | 2 | 3 | 4 |
| --- | --- | --- | --- |
| 3~20$_{kg/cm^2}$ | Atmospheric Pressure | Atmospheric Pressure | Atmospheric Pressure |
| 50~100° C. | 50~80° C. | Room Temperature | −10~20° C. |
| 1~5 hours | 4~24 hours | 4~24 hours | 1~3 days |

If necessary, it is preferable to stir the reaction solution to facilitate the cleavage. Particularly, according to the present invention, a good cleavage yield of more than 90% can be obtained by stirring for 1 to 3 days even if the temperature is as low as −20° C. (see, condition 4 in Table 1).

The waste siloxane bond-containing compound which is to be used as a material in the decomposition process according to the present invention includes discarded silicone rubber, silicone resin and silica. The wastes may be used in the form of mass, but they also be finely cut or ground into powder before use. Preferably, wastes having 0.5 to 10 mm of particle diameter, more preferably, those having 3 mm or less of particle diameter are used upon considering the cleavage yield.

After the cleavage reaction is completed, neutralization and heating were proceeded to obtain silicone oil of a low molecular weight and siloxylated silica having about 10 to 100 μm of particle diameter. The cleavage process for polyorganosiloxane compound and silica are depicted in the following reaction schemes 3 and 4, respectively.

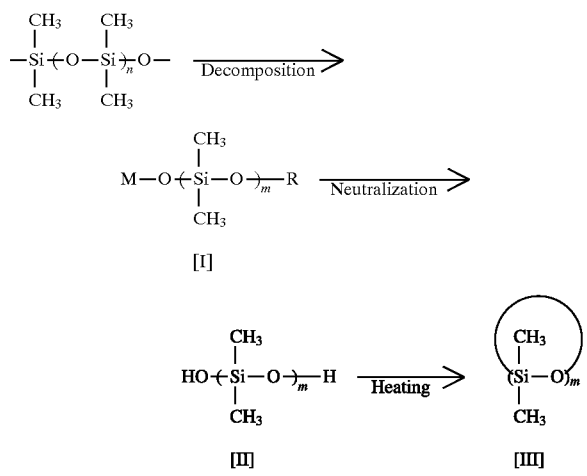

in which

R represents alkali metal or $C_1$–$C_{10}$ alkyl,

M represents alkali metal, n denotes an integer of 10 to 40, and m denotes an integer of 2 to 6.

The process described in the above reaction scheme 3 will be more specifically explained below. The decomposition product [I] obtained from cleavage reaction is filtered and the residue is washed with polar or nonpolar organic solvent. The filtrate and the washings are mixed together. After the organic solvent contained in the mixture is removed by distillation under reduced pressure, the residue is neutralized by the addition of inorganic acid, preferably hydrochloric acid. The organic substance in the upper layer is collected and washed with distilled water. The solvent contained therein is eliminated by distillation under reduced pressure to obtain the compound of formula [II] which contains both the terminal hydroxy group and siloxane bond. The resulting compound [II] is heated for 30 minutes to 4 hours at 120 to 170° C. to obtain the compound of formula [III] as a cyclic decomposition product in which the terminal hydroxy group is absent and only the siloxane bond is contained. The compound [III] is a silicone oil having an average molecular weight of 300 to 500. On the other hand, siloxylated fine silica (particle diameter of about 10 to 100 μm) is obtained by neutralizing, washing and drying the residue resulted from filtration. Herein, the "siloxylated silica" means that polyorganosiloxane compound is attached to the surface of the solid silica.

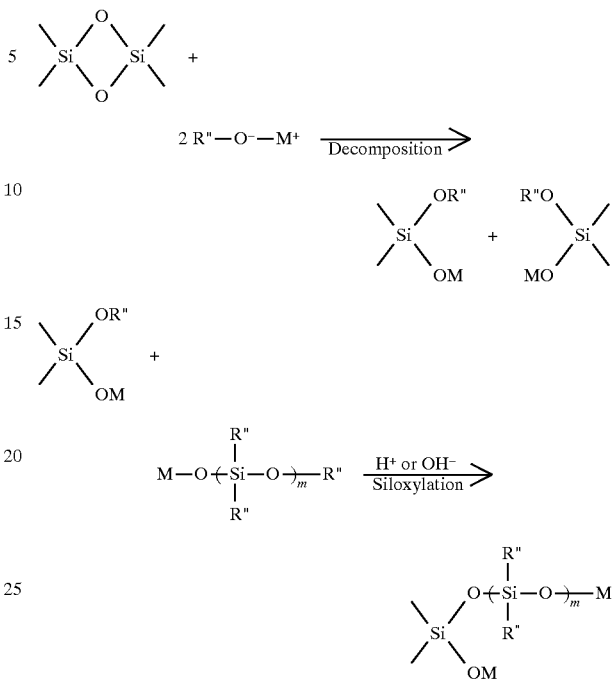

in which

R" represents $C_1$–$C_{10}$ alkyl,

M represents alkali metal, and m denotes an integer of 2 to 6.

According to the cleavage process as explained above, the siloxane bond-containing compound can be decomposed with a good yield under conditions of low temperature and atmospheric pressure. If silicone oil having a lower molecular weight and minuter silica are desired, however, the decomposition product obtained from the above cleavage process should be sonicated and treated by a terminator of triorganylhalosilane represented by the following formula [IV] after an alkali decomposer and a decomposition facilitator are introduced into the reaction system.

$$\begin{array}{c} R_1 \\ | \\ R_2-Si-X \\ | \\ R_3 \end{array} \qquad [IV]$$

in which $R_1$, $R_2$ and $R_3$ independently of one another represent $C_1$–$C_6$ alkyl, or phenyl or vinyl which is optionally substituted, and X represents halogen, preferably chlorine.

That is, the present invention also relates to a process for decomposing siloxane bond-containing compound characterized in that the siloxane bond-containing compound is decomposed by an alkali decomposer in the presence of one or more selected from a group consisting of secondary and tertiary aliphatic alcohols are used as a decomposition facilitator and then the decomposition product is sonicated and treated with a triorganylhalosilane of formula [IV] after the decomposer and the decomposition facilitator are further introduced into the reaction system.

The latter cleavage process will be more specifically explained below. As the material to be treated in the latter process, the decomposition product obtained in the former cleavage reaction is used. Time to further introduce the decomposer and decomposition facilitator into the decomposition product in order to carry out the latter process is not restricted, and any appropriate step before or after filtration, or before or after neutralization may optionally be selected.

The decomposers and the decomposition facilitators mentioned for the former cleavage reaction can also be used in the latter cleavage process, however, it is not necessary to use the same decomposers and decomposition facilitators in the latter process as those used in the former process. The preferable amounts of decomposer and decomposition facilitator with respect to the material are identical to those mentioned for the former process.

Sonication is performed at a temperature of less than room temperature, preferably at 0 to 5° C., for 10 to 30 minutes under conditions of 16 to 30 kHz and 0.5 to 2 kW in the presence of a decomposer and a decomposition facilitator. After the sonication is completed, the sonication product is treated with the triorganylhalosilane of formula [IV] as a terminator in an anhydrous nonpolar solvent optionally in the presence of an acid.

As the acid which can be used in the termination reaction, inorganic acid, preferably hydrochloric acid, nitric acid or sulfuric acid, particularly preferably hydrochloric acid can be mentioned. Any conventional nonpolar solvent in the field of organic synthesis can be used in the present reaction if it does not adversely affect the reaction. The solvent is used in alone or mixed with other one or more solvents. In the present reaction system, anhydrous nonpolar solvents should be used because the alkoxide(-OR) or the metal oxide(-OM) group present at both terminals of the decomposition product may be dissociated into hydroxide and subsequently dehydration and condensation reactions may occur in the presence of water. As the specific examples for the triorganylhalosilane of formula [IV], trialkylhalosilane, dialkylmonophenylhalosilane, dialkylmonovinylhalosilane, monoalkyldiphenylhalosilane, monoalkyldivinylhalosilane, triphenylhalosilane, diphenylmonovinylhalosilane, monophenyldivinylhalosilane or alkylphenylvinylhalosilane can be mentioned. Among them, one or more selected from a group consisting of trimethylchlorosilane, triethylchlorosilane, triphenylchlorosilane, dimethylethylchlorosilane, diethylmethylchlorosilane, methylvinylphenylchlorosilane, ethylvinylchlorosilane, divinylmethylchlorosilane, divinylethylchlorosilane and divinylphenylchlorosilane are preferably used, and one or more selected from a group consisting of trimethylchlorosilane, triethylchlorosilane and triphenylchlorosilane are most preferably used. When the acid is used in the termination reaction, it can be applied in amounts ranging from 1 to 10 times by volume with respect to the triorganyihalosilane according to the purpose.

It is understood that the decomposition mechanism of polyorganosiloxane compound in the latter cleavage process, in which sonication and treatment by a terminator are carried out, is proceeded as in the following reaction scheme 5. Also, it is thought that the siloxylated silica obtained from the former cleavage process may be reacted with the triorganylhalosilane as in the following reaction scheme 6. If the siloxylated silica is treated with an acid such as hydrochloric acid instead of the triorganylhalosilane in reaction scheme 6, hydroxy groups remain at both terminals.

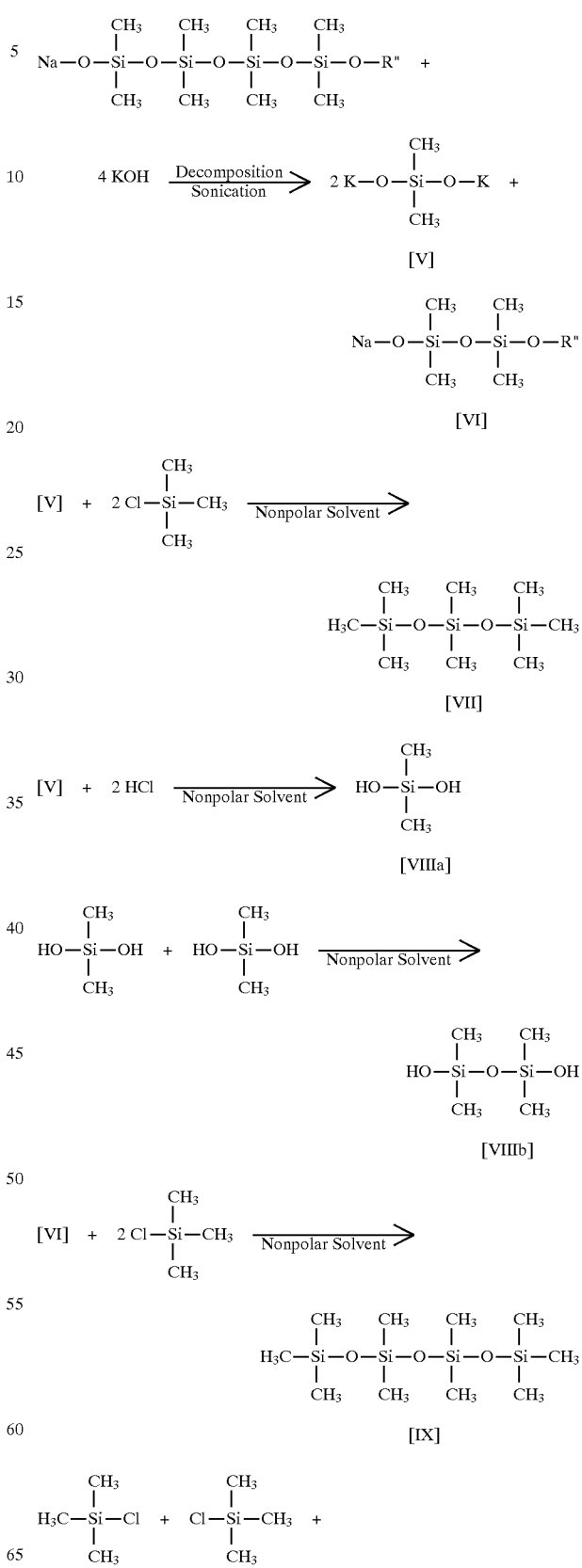

-continued
Reaction Scheme 5

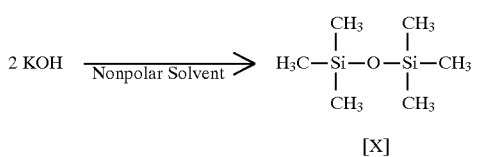

[X]

in which
R" represents $C_1$–$C_{10}$ alkyl.

Reaction Scheme 6

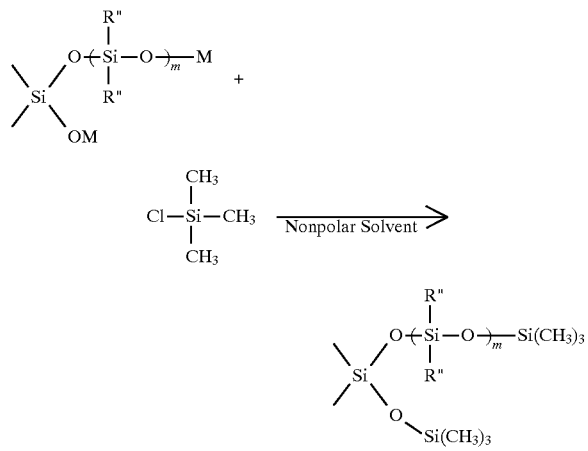

in which
R" represents $C_1$–$C_{10}$ alkyl,
M represents alkali metal, and
m denotes an integer of 2 to 6.

After the latter cleavage reaction is completed, conventional work-up processes such as filtration, centrifugation, distillation under reduced pressure, etc. may be carried out to obtain the desired oily compound which has a variety of polymerization degree and contains terminal hydroxy groups and siloxane bonds. This silicone oil may be recovered as it is or may be heated for 30 minutes to 4 hours at 120 to 170° C. to recover a silicone oil which has an average molecular weight of 150 to 300 and in which terminal hydroxy groups are absent and siloxane bonds are retained. While, it is possible to obtain still more micronized siloxylated silica (particle diameter of less than 1 μm) than the silica obtained from the former cleavage process if the solid residue obtained through the latter cleavage reaction, washing with distilled water, filtration, centrifugation, etc. is dried under reduced or atmospheric pressure at temperatures ranging from 100 to 110° C.

In the latter cleavage process, the product resulted from the first sonication may be sonicated secondarily in the presence of a terminator. Whether or not the secondary sonication is performed depends on the materials used or reaction conditions, and it can be easily determined by a person skilled in this art.

As explained above, the present invention has some characteristics such that secondary and/or tertiary aliphatic alcohols are used as a decomposition facilitator in the process for decomposing siloxane bond-containing compound by alkali decomposer, and that the decomposition product is sonicated and treated with a terminator in the optional subsequent process. Due to its unique constitutional characteristics, the present invention exhibits a superior effect in cleavage rate and yield to that of the existing cleavage processes by alkali.

The process for decomposition according to the present invention can be applied to a rubber composition prepared by combining synthetic rubber and polyorganosiloxane compound. The silicone oil obtained from the decomposition can be advantageously used in the preparation of silicone rubber, insulating oil, lubricating oil having a low viscosity, engine oil, modifier having a high molecular weight, fiber processing agent, water repellent, additive for cosmetics, varnish, parting agent, surface treatment, vacuum pump oil, functional treatment, pinch-off oil, gloss agent, etc. The siloxylated silica can be effectively used as reinforcing filler for various rubbers including silicone rubber, developing agent of agricultural chemicals, pigment, anti-precipitating agent for printing ink, gloss-removing agent, additive for cosmetics, etc.

The present invention will be more specifically explained by the following examples. However, it should be understood that the examples are intended to illustrate but not to in any manner limit the scope of the present invention. Unless otherwise stated, aliphatic alcohols having a purity of 98% or more are used in the following examples.

Reference Example 1

100 ml of octamethylcyclotetrasiloxane, 5 ml of tetramethylammonium hydroxide[$(CH_3)_4NOH$] and 50 ml of benzene were introduced into a reaction flask equipped with a refluxing condenser, a stirrer and a thermometer, and the reaction mixture was heated for 5 hours at 100° C. Tetramethylammonium hydroxide was removed again by heating the mixture at 130° C. to prepare 70 g of crude silicone rubber having a molecular weight of 15,000 or more. 50 g of fumed silica having an average particle diameter of 73.72 μm (diameter range: about 10 to 500 μm, specific surface area: 0.1137 $m^2$/gm, see FIG. 1) was combined with 50 g of the crude silicone rubber thus obtained. A mixture of 1 g of benzoyl peroxide, 5 ml of octamethylcyclotetrasiloxane and 20 ml of diethylether was added thereto and then the whole mixture was matured in a refrigerator of 5 to 10° C. Then, the silicone rubber thus produced was vulcanized by heating for 2 hours at 170° C. and 200° C., respectively. This vulcanized silicone rubber was used as a material in the following examples.

EXAMPLE 1

(a) Cleavage of silicone rubber and recovery of silicone oil 100 g of the silicone rubber prepared in Reference Example 1 was introduced into an autoclave equipped with a stirrer, a mixture of 100 ml of isopropanol and 100 ml of methanol was added thereto and then the reaction mixture was stirred for 30 minutes. After 15 g (0.37 mole) of sodium hydroxide was added to the reaction mixture, the autoclave was sealed. The mixture contained in the autoclave was stirred for 2 hours under conditions of inner pressure 6±2 kg/$cm^2$ and temperature 60±10° C. in order to carry out the cleavage reaction. Then, the reaction solution was cooled down to room temperature, the decomposition product was filtered by suction and the resulting residue was washed with n-hexane 5 times. The filtrate and the washings were combined and then n-hexane, isopropanol and methanol contained therein were removed under reduced pressure in a rotary evaporator. The residue was cooled down to room temperature, introduced into a separatory funnel and then neutralized with 5N aqueous hydrochloric acid solution. The organic substance in the upper layer was thoroughly washed with distilled water and dried over anhydrous sodium sulfate. Then, the organic solvent remained was eliminated under reduced pressure at a temperature of 50° C. or less.

Figure 2:
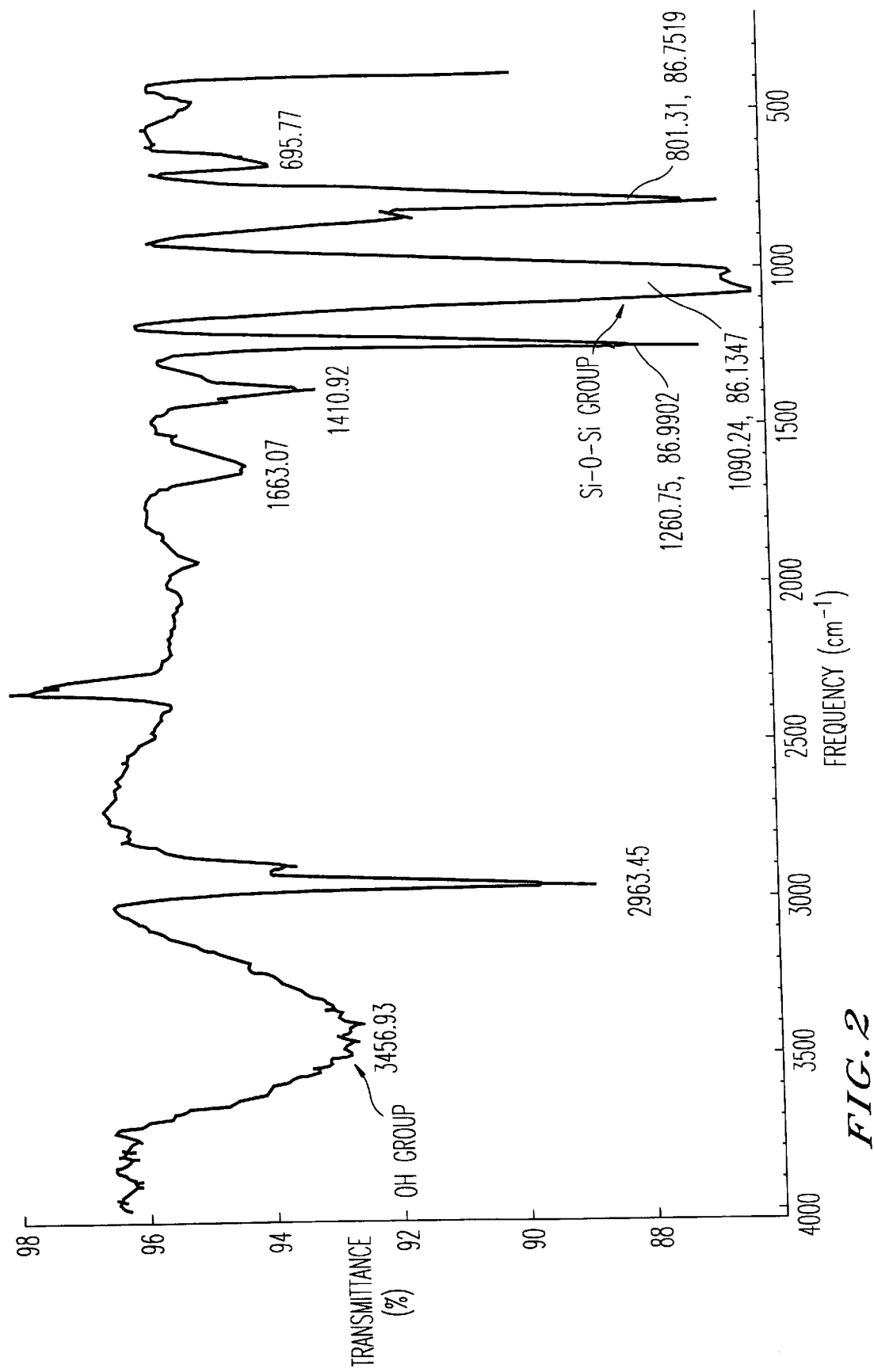
FIG. 2 represents the IR spectrum to identify the presence of hydroxy group and siloxane bond in the silicone oil obtained before heat treatment for 3 hours under conditions of atmospheric pressure and 150° C. in Example 1.
Figure 3:
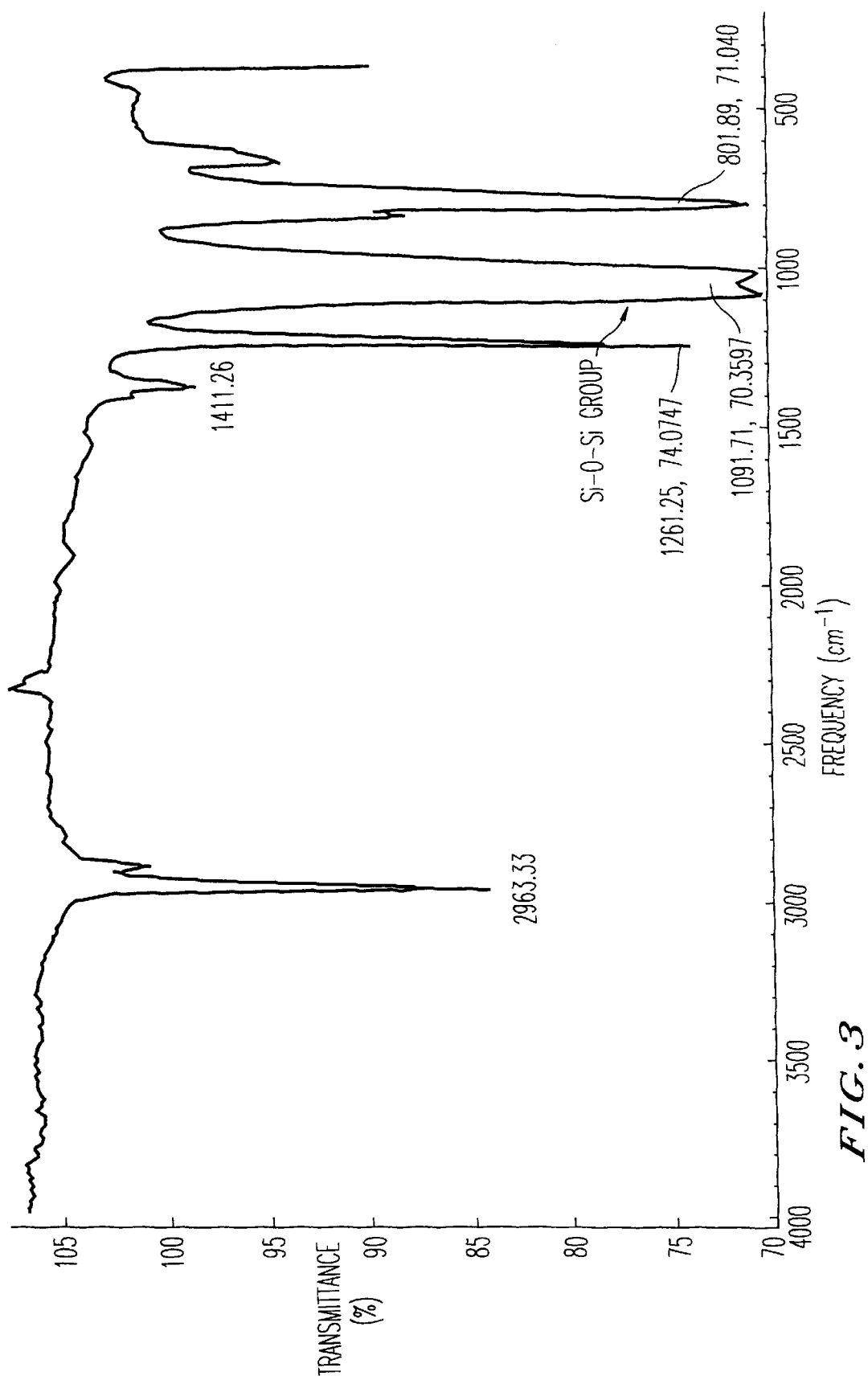
FIG. 3 represents the IR spectrum to identify the absence of hydroxy group and the presence of siloxane bond in the silicone oil obtained after heat treatment for 3 hours under conditions of atmospheric pressure and 150° C. in Example 1.

Since the resulting residue contained terminal hydroxy groups and siloxane bonds (see, IR absorption spectrum of FIG. 2), it was heated for 3 hours at 150° C. under atmospheric pressure to obtain 45 g (Yield 90%; this is a decomposition yield with respect to the weight of silicone rubber and the following yields should be understood equally) of silicone oil in which the terminal hydroxy groups were absent and siloxane bonds were contained (see, FIG. 3).

(b) Recovery of siloxylated silica powder

Figure 4:
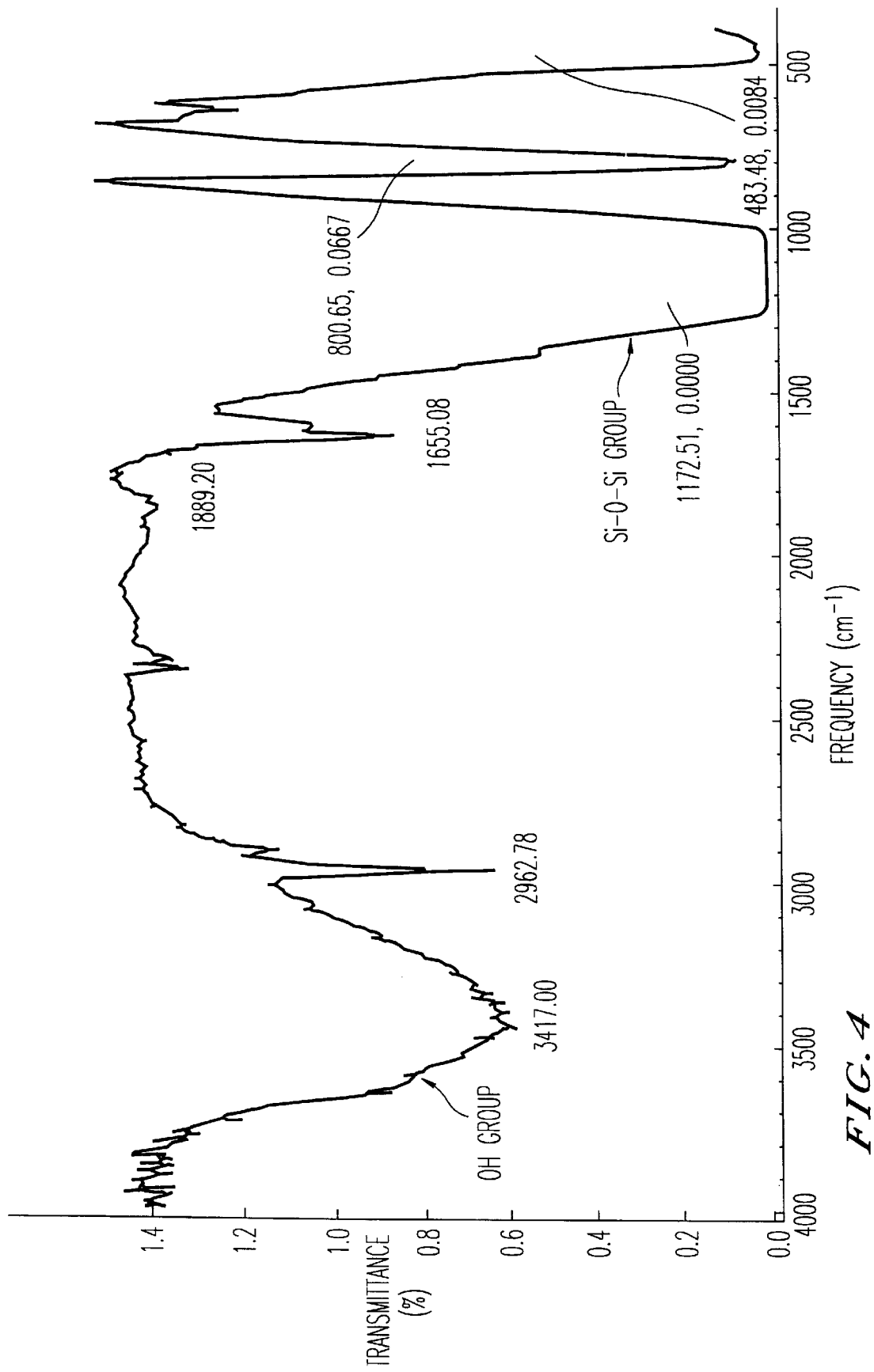
FIG. 4 represents the IR spectrum to identify the presence of hydroxy group and siloxane bond on the surface of the silica powder obtained before drying for 2 hours at 120° C. in Example 1.
Figure 5:
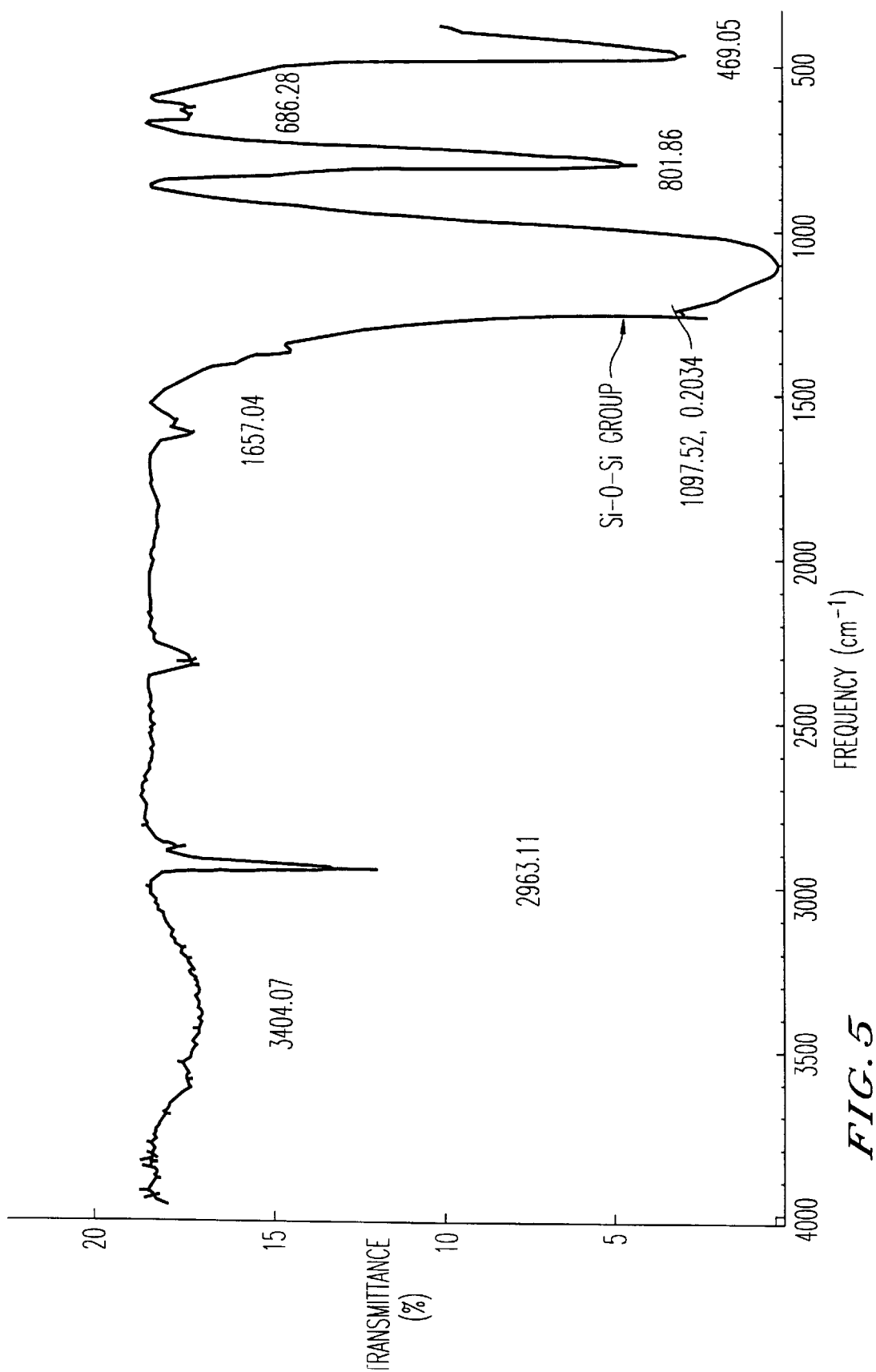
FIG. 5 represents the IR spectrum to identify the absence of hydroxy group and the presence of siloxane bond on the surface of the silica powder obtained after drying for 2 hours at 120° C. in Example 1.
Figure 6:
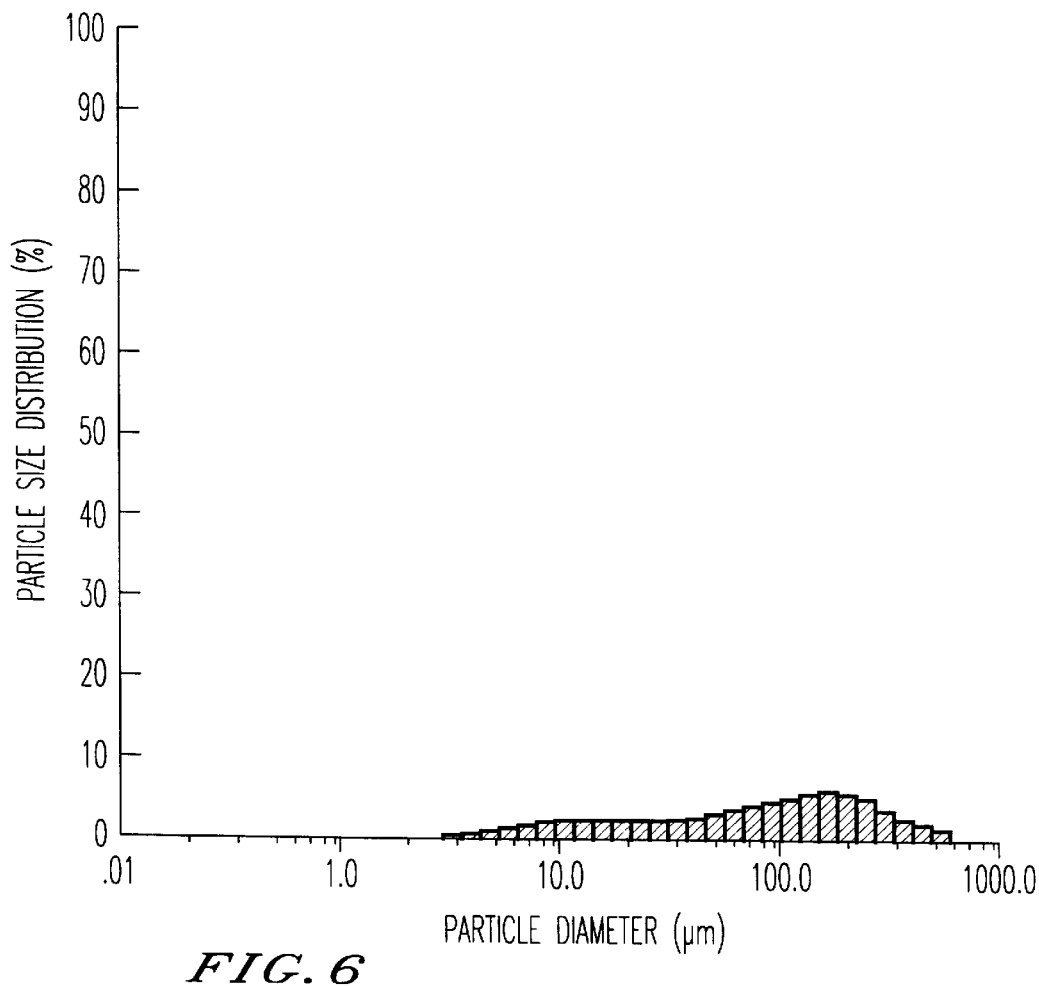
FIG. 6 represents the particle size analysis diagram of the siloxylated silica obtained in Example 1.

The residue obtained after filtration in (a) was washed with n-hexane 5 times, neutralized with 5N aqueous hydrochloric acid solution and then washed with distilled water 5 times. The washed residue was dried under reduced pressure at 50° C. to obtain powder which was identified by IR analysis to have hydroxy groups and siloxane groups attached to the surface thereof (see, FIG. 4). This powder sample was dried for 2 hours at 120° C. to obtain 52 g of silica which was identified by IR analysis to have siloxane groups only on the surface thereof and hydroxy groups were eliminated therefrom(see, FIG. 5). The siloxylated silica thus obtained was analyzed by the method as represented below, and as a result it was identified to have an average particle diameter of 87.40 $\mu$m (diameter range: 1.6~600 $\mu$m, specific surface area: 0.2697 $m^2$/gm, see FIG. 6).

Conditions for Analysis of Particle Size

Instrument: Mastersizer X (Malvern Instruments Co., England)

Principles: laser diffraction using Mie theory, light scattering and back scattering Dispersing Medium: distilled water Detector: single chip silicon photodiode array (multi element detector: 31 channel)

Wavelength: He—Ne laser, wavelength 632.8 nm, 5 mW

Procedure: Specific amount of sample is dispersed in distilled water, stirred for 30 minutes and simultaneously sonicated (36 kHz, 60 watt).

Then, the sample is analyzed under the above mentioned conditions.

(c) Molecular Weight Analysis of Silicone oil

Figure 7:
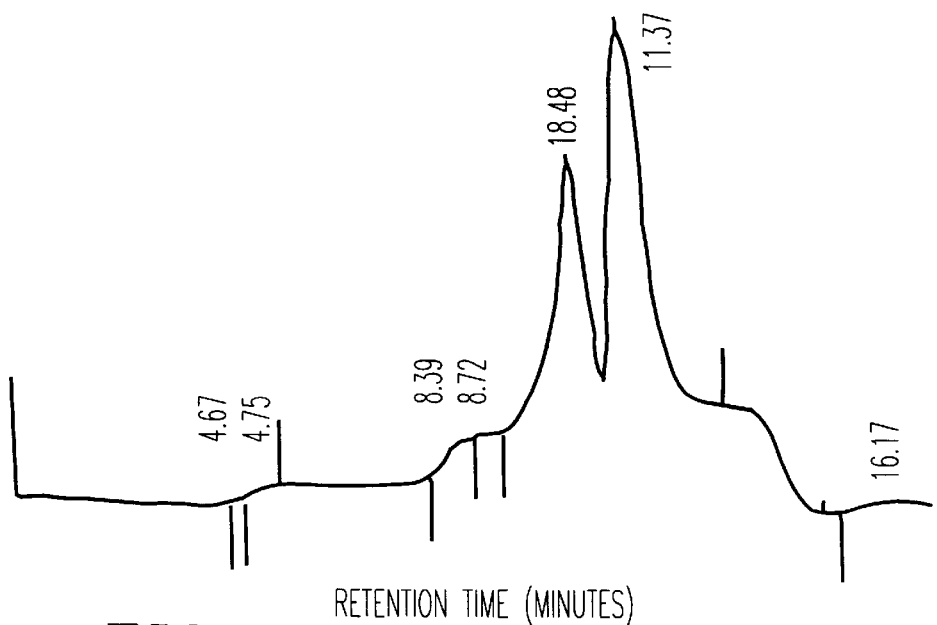
FIG. 7 represents the gel filtration chromatogram of the silicone oil obtained in Example 1.
Figure 8:
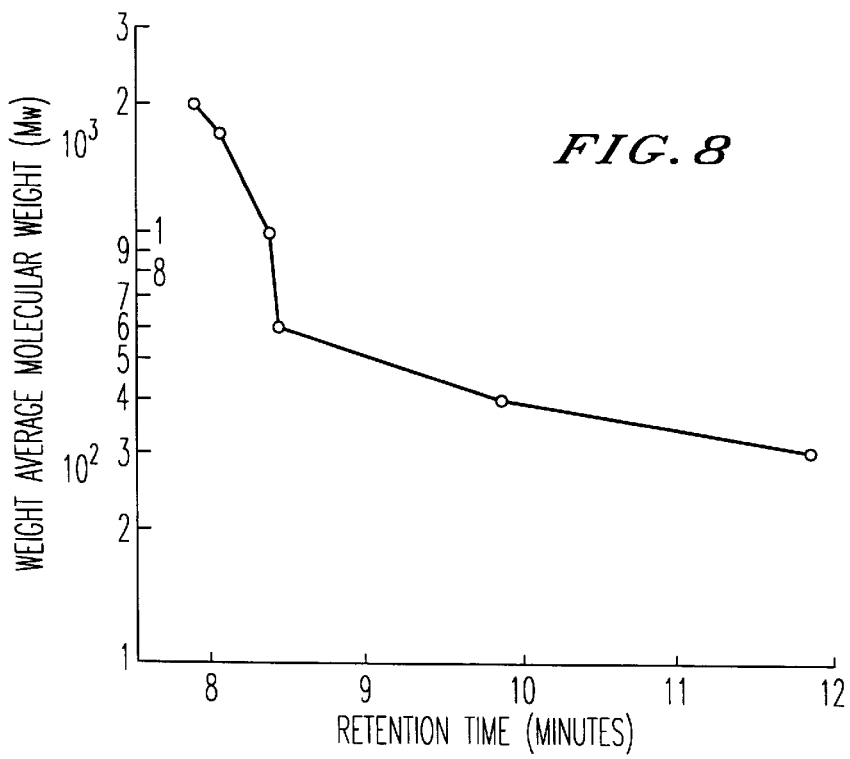
FIG. 8 represents the calibration curve of polystyrene as a molecular weight marker.

The silicone oil obtained in (a) was subjected to gel filtration chromatography under the conditions as mentioned below. The chromatogram thus obtained (FIG. 7) was compared with the calibration curve of molecular weight marker (FIG. 8), from which it was identified that the weight average molecular weight of the silicone oil is 360 (molecular weight range: 350~400).

Column: Waters Styragel TM 10 Å and 100 Å combined serially

Temperature: 25° C.

Eluent: chloroform

Detector: UV 245 nm

Molecular Weight Marker Sample: polystyrene (molecular weight 2000, 1800, 1000, 600, 400, 300)

Flow Rate: 1.6 ml/min

It can be seen from the result of the present example that the amount of silicone oil obtained by cleavage reaction is lower than 50 g which is the amount of material rubber, and that the amount of silica recovered is higher than 50 g which is the amount of fumed silica combined first. It Is considered that this is because parts of the decomposition product and the material not decomposed, each of which contains siloxane groups and/or terminal hydroxy groups, are attached to the surface of the recovered silica. Accordingly, the particle size distribution range of the recovered silica has been upwardly readjusted a little.

EXAMPLE 2

The same procedure as Example 1 was carried out except that methanol was not used and instead 200 ml of isopropanol was used alone in the cleavage reaction to obtain 40 g (Yield 80%) of silicone oil having an average molecular weight of 470 (molecular weight range: 450~500) and 55 g of siloxylated silica having an average particle diameter of 86.98 $\mu$m.

EXAMPLE 3

100 g of silicone rubber prepared in Reference Example 1 was finely cut in a size of 1 to 3 mm, introduced into a 1 l three necked flask equipped with a refluxing condenser and a stirrer and then 300 ml of isopropanol and 40 g (1 mole) of sodium hydroxide were added thereto. The mixture was stirred for 15 hours under conditions of room temperature and atmospheric pressure to decompose the silicone rubber. Then, the decomposition product was filtered by suction and the residue thus obtained was washed with n-hexane 5 times. The filtrate and the washings by n-hexane were combined and then n-hexane and isopropanol contained therein were removed under reduced pressure in a rotary evaporator. The residue was introduced into a separatory funnel and then neutralized with 5N aqueous hydrochloric acid solution. The organic substance in the upper layer was thoroughly washed with distilled water and dried over anhydrous sodium sulfate. Then, the organic solvent remained was eliminated under reduced pressure. The resulting residue was heated for 3 hours at 150° C. under atmospheric pressure to obtain 45.2 g (Yield 90.4%) of silicone oil having an average molecular weight of 360 (molecular weight range: 350~400; determined by gel filtration column chromatography) in which the terminal hydroxy groups were absent and siloxane bonds were contained.

The residue obtained after washing with n-hexane(5 times) was treated according to the same procedure as Example 1 to prepare 50 g of siloxylated silica having an average particle diameter of 87.43 $\mu$m.

EXAMPLE 4

150 ml of isopropanol, 150 ml of methanol and 15 g (0.375 mole) of sodium hydroxide were introduced into a 1 l double neck flask equipped with a refluxing condenser and a stirrer and then they were dissolved and cooled down to room temperature. 100 g of silicone rubber prepared in Reference Example 1 was finely cut in a size of 1 to 3 mm and then added thereto. The mixture was stirred for 16 hours to decompose the silicone rubber. The decomposition product was filtered by suction and the residue thus obtained was washed with a mixture of n-hexane and methanol (1/1, v/v) 5 times. The filtrate and the washings were combined and then n-hexane, isopropanol and methanol contained therein were removed under reduced pressure in a rotary evaporator. The residue was cooled down to room temperature, introduced into a separatory funnel and then neutralized with 5N aqueous hydrochloric acid solution. The organic substance in the upper layer was thoroughly washed with distilled water 5 times and dried over anhydrous sodium sulfate. Then, the organic solvent remained was eliminated under reduced pressure. The resulting residue was heated for 3 hours at 150° C. under atmospheric pressure to obtain 46 g (Yield 92%) of silicone oil having an average molecular weight of 360 (molecular weight range: 350~400; determined by gel filtration column chromatography) in which the terminal hydroxy groups were absent and siloxane bonds were contained.

The residue obtained after washing with a mixture of n-hexane and methanol (5 times) was treated according to the same procedure as Example 1 to prepare 51 g of siloxylated silica having an average particle diameter of 87.13 μm.

EXAMPLE 5

The same procedure as Example 4 was carried out except that 20 g (0.357 mole) of potassium hydroxide instead of sodium hydroxide was used in the cleavage reaction and the cleavage time was adjusted to 10 hours to obtain 46 g (Yield 92%) of silicone oil having an average molecular weight of 360 (molecular weight range: 350~400) and 51 g of siloxylated silica having an average particle diameter of 87.36 μm.

EXAMPLE 6

The same procedure as Example 4 was carried out except that 100 ml of n-hexane was additionally used in the cleavage reaction and the cleavage time was adjusted to 13 hours to obtain 45 g (Yield 90%) of silicone oil having an average molecular weight of 360 (molecular weight range: 350~400) and 52 g of siloxylated silica having an average particle diameter of 87.59 μm.

EXAMPLE 7

The same procedure as Example 6 was carried out except that 20 g (0.357 mole) of potassium hydroxide instead of sodium hydroxide was used in the cleavage reaction and the cleavage time was adjusted to 8 hours to obtain 46 g (Yield 92%) of silicone oil having an average molecular weight of 370 (molecular weight range: 350~400) and 51 g of siloxylated silica having an average particle diameter of 87.45 μm.

EXAMPLE 8

The same procedure as Example 6 was carried out except that 7 g (0.125 mole) of potassium hydroxide was used together with 10 g (0.25 mole) of sodium hydroxide in the cleavage reaction and the cleavage time was adjusted to 6 hours to obtain 47 g (Yield 94%) of silicone oil having an average molecular weight of 360 (molecular weight range: 350~400) and 50 g of siloxylated silica having an average particle diameter of 87.39 μm.

EXAMPLE 9

The same procedure as Example 8 was carried out except that 150 ml of 2-butanol was used instead of isopropanol in the cleavage reaction and the cleavage time was adjusted to 7 hours to obtain 46 g (Yield 92%) of silicone oil having an average molecular weight of 360 (molecular weight range: 350~400) and 51 g of siloxylated silica having an average particle diameter of 87.49 μm.

EXAMPLE 10

50 g of the residue obtained before the neutralization with 5N aqueous hydrochloric acid solution in Example 4 was introduced into a 1 l plastic beaker and then a mixture of 20 g (0.5 mole) of sodium hydroxide, 150 ml of isopropanol and 100 ml of methanol was added thereto. The reaction mixture was sonicated for 10 minutes under conditions of 20 kHz and 1 kW while the temperature was maintained to 0 to 5° C. The reaction solution sonicated was treated with 40 ml of trimethylchlorosilane and 100 ml of dry diethylether. The whole mixture was introduced into a separatory funnel, thoroughly washed with distilled water and then the organic layer was separated. After the organic solvent contained therein was removed by distillation under reduced pressure, the residue was heated for 3 hours at 150° C. to obtain 70 g of silicone oil having an average molecular weight of 280 (molecular weight range: 150~300)

EXAMPLE 11

Figure 9:
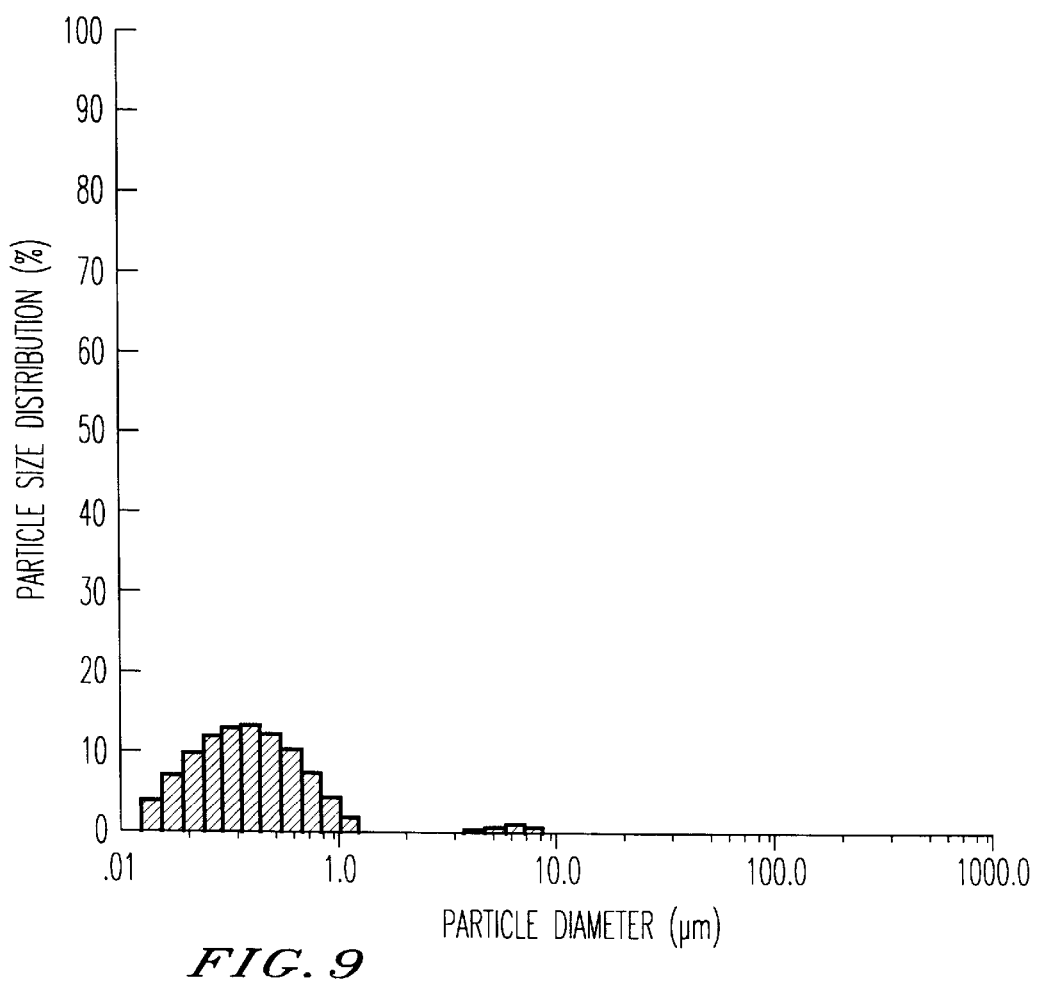
FIG. 9 represents the particle size analysis diagram of the siloxylated silica obtained in Example 11.

50 g of the residue obtained after washing with a mixture of n-hexane and methanol in Example 4 was introduced into a 200 ml plastic beaker and then 10 g (0.178 mole) of potassium hydroxide and 100 ml of isopropanol were added thereto. The reaction mixture was sonicated for 20 minutes under conditions of 20 kHz and 1 kW while the temperature was maintained to 0 to 5° C. A mixture of 30 ml of trimethylchlorosilane and 50 ml of dry diethylether was added to the reaction solution sonicated and then the resulting mixture was sonicated for further one minute under the same conditions. The mixture was thoroughly washed with distilled water and then centrifuged for 6 minutes at 17,400×g to collect the precipitate. The precipitate was dried for one day in an oven of 105° C. to obtain 41 g of siloxylated solid silica powder. This siloxylated silica was analyzed according to the same procedure as Example 1 to have an average particle diameter of 0.38 μm (diameter range: 0.10~1.25 μm, specific surface area: 7.5055 m$^2$/gm, see FIG. 9).

EXAMPLE 12

Figure 10:
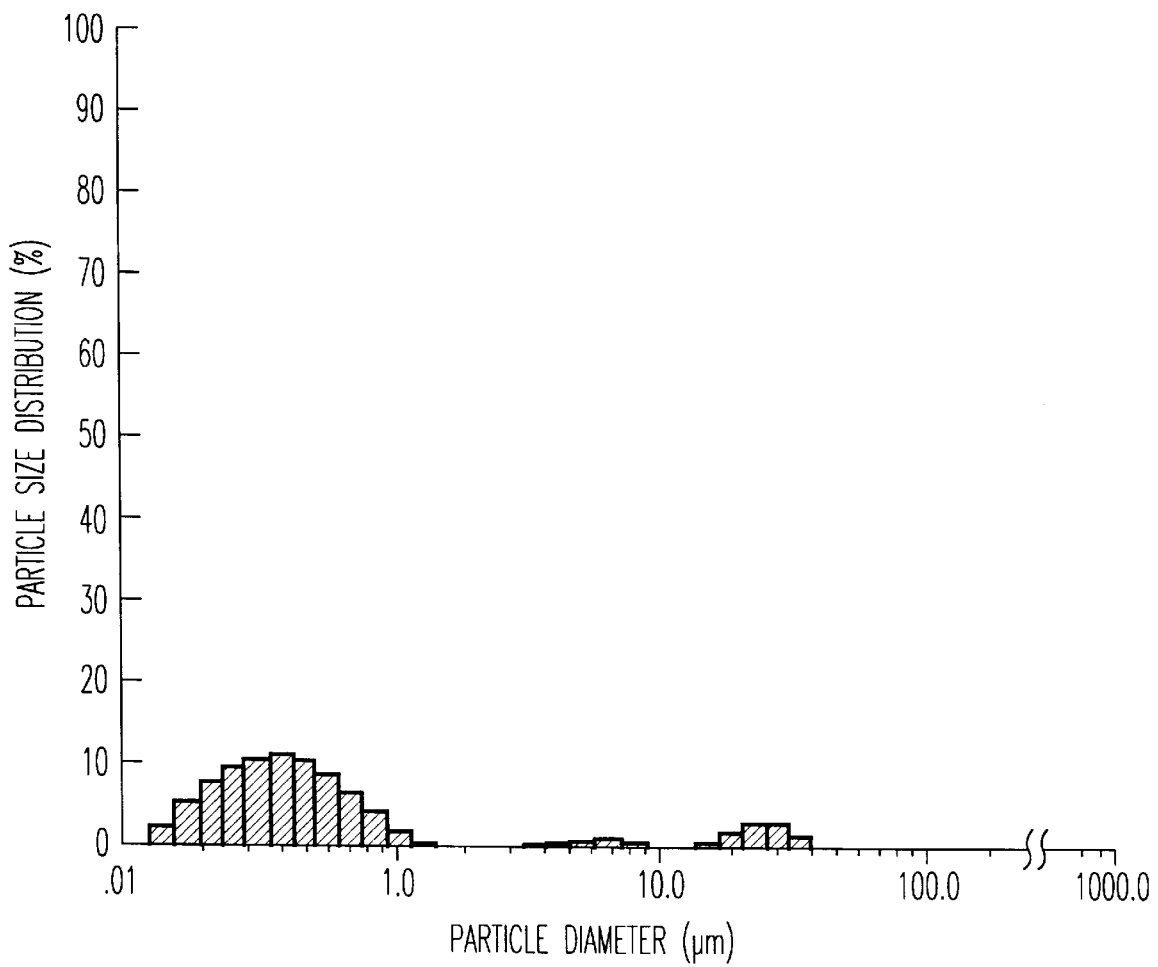
FIG. 10 represents the particle size analysis diagram of the siloxylated silica obtained in Example 12.

The same procedure as Example 11 was carried out except that a mixture of trimetliylchlorosilane and hydrochloric acid (4/1, v/v) was used instead of trimethylchlorosilane to obtain 41 g of siloxylated solid silica powder having an average particle diameter of 0.44 μm (diameter range: 0.10~1.50 μm, specific surface area: 6.3250 m$^2$/gm, see FIG. 10).

EXAMPLE 13

100 g of the decomposition product obtained before the filtration in Example 4 was introduced into a 1 l plastic beaker and then 20 g (0.36 mole) of potassium hydroxide and 50 ml of isopropanol were added thereto. The reaction mixture was sonicated for 20 minutes under conditions of 20 kHz and 1 kW while the temperature was maintained to 0 to 5° C. The reaction solution sonicated was centrifuged for 6 minutes at 17,400×g to collect the supernatant. The supernatant was neutralized by 5N aqueous hydrochloric acid solution, washed with distilled water, dried, distilled under reduced pressure to remove the organic solvent and heated for 3 hours at 150° C. according to the same procedure as Example 1 except that 100 ml of n-hexane was added to obtain 45 g (Yield 90%) of silicone oil having an average molecular weight of 360 (molecular weight range: 350~500).

Figure 11:
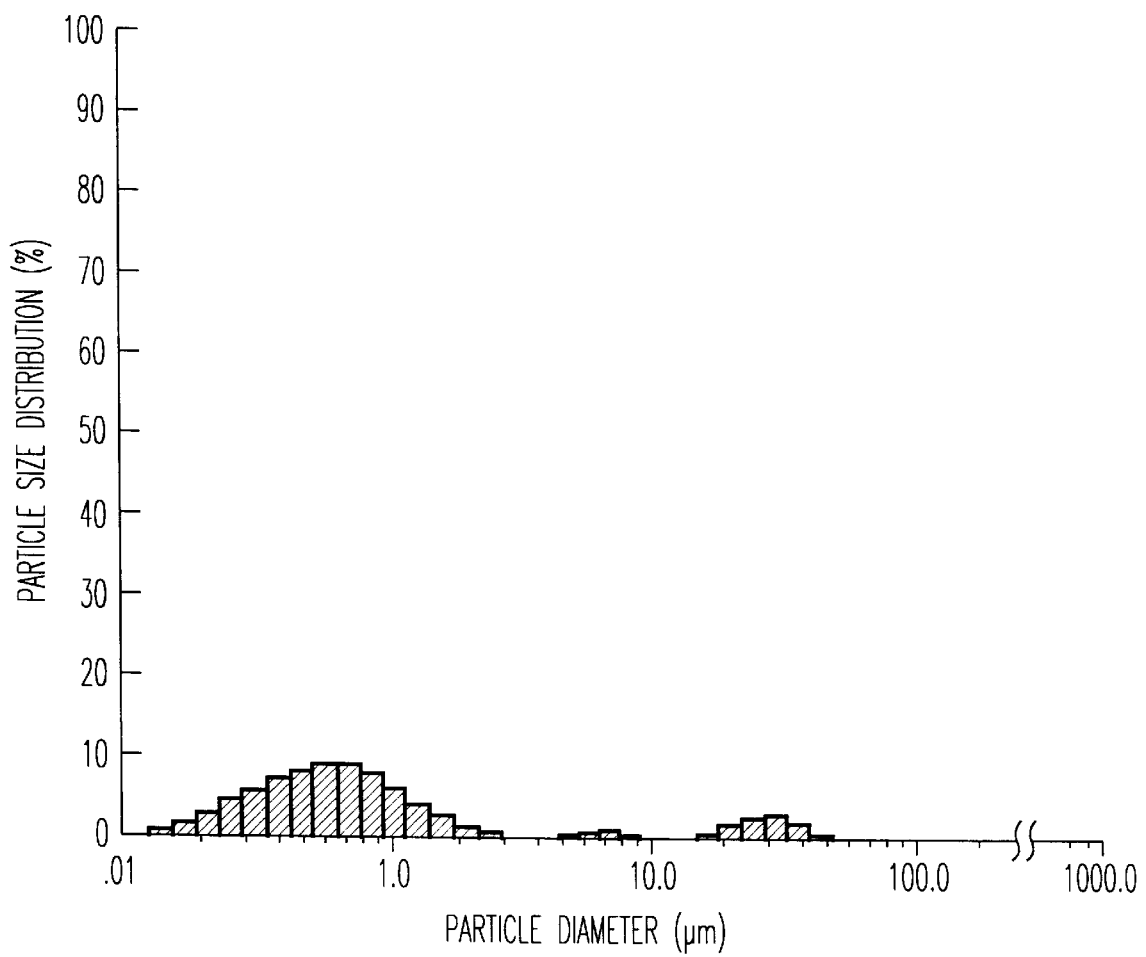
FIG. 11 represents the particle size analysis diagram of the siloxylated silica obtained in Example 13.

The precipitate obtained after centrifugation was treated according to the same procedure as Example 11 to prepare 11 g of siloxylated solid silica powder having an average particle diameter of 0.77 μm (diameter range: 0.1~3.0 μm, specific surface area: 4.103 m$^2$/gm, see FIG. 11).

EXAMPLE 14

The following experiment was carried out to identify whether the surface of silica which is not ground is siloxylated or not when the silica is treated with the decomposition product obtained in Example 4.

The decomposition product obtained before filtration in Example 4 was introduced into 2 l polyethylene flask and then 100 g of fumed silica (see, FIG. 1) which is commonly used as a reinforcing filler for silicone rubber, 200 ml of isopropanol and 200 ml of methanol were added thereto. The mixture was stirred for 30 minutes in a water bath of 50~60° C. and subsequently refluxed while heating to a temperature of 60° C. or more for one hour. The mixture was cooled down to room temperature while stirring. The reaction solution was filtered by suction to obtain a solid, which is then washed with methanol 5 times to remove any rubber remained. The solid was neutralized with 5N aqueous hydrochloric acid solution and washed with distilled water to remove the hydrochloric acid remained. The washed solid was dried for 10 hours at 105±5° C. and then heated for one hour at 150~170° C. to obtain 151 g of siloxylated silica having an average particle diameter of 73 μm (diameter range: 70~100 μm). While, the filtrate and washings with methanol were combined and then solvents such as methanol, isopropanol, etc. were removed in a rotary evaporator. The residue was cooled down to room temperature, neutralized by 5N aqueous hydrochloric acid solution and then washed with distilled water to remove the hydrochloric acid remained. 100 ml of n-hexane was added thereto and the supernatant (n-hexane layer) was taken. The n-hexane contained in the supernatant was removed under reduced pressure and the resulting residue was heated for 3 hours at 130~150° C. to obtain 40 g (Yield 80%) of silicone oil having an average molecular weight of 360 (molecular weight range: 350~400).

EXAMPLE 15

The following experiment was carried out to identify whether the surface of ground silica is siloxylated or not when the silica is treated with the decomposition product obtained in Example 4.

Figure 12:
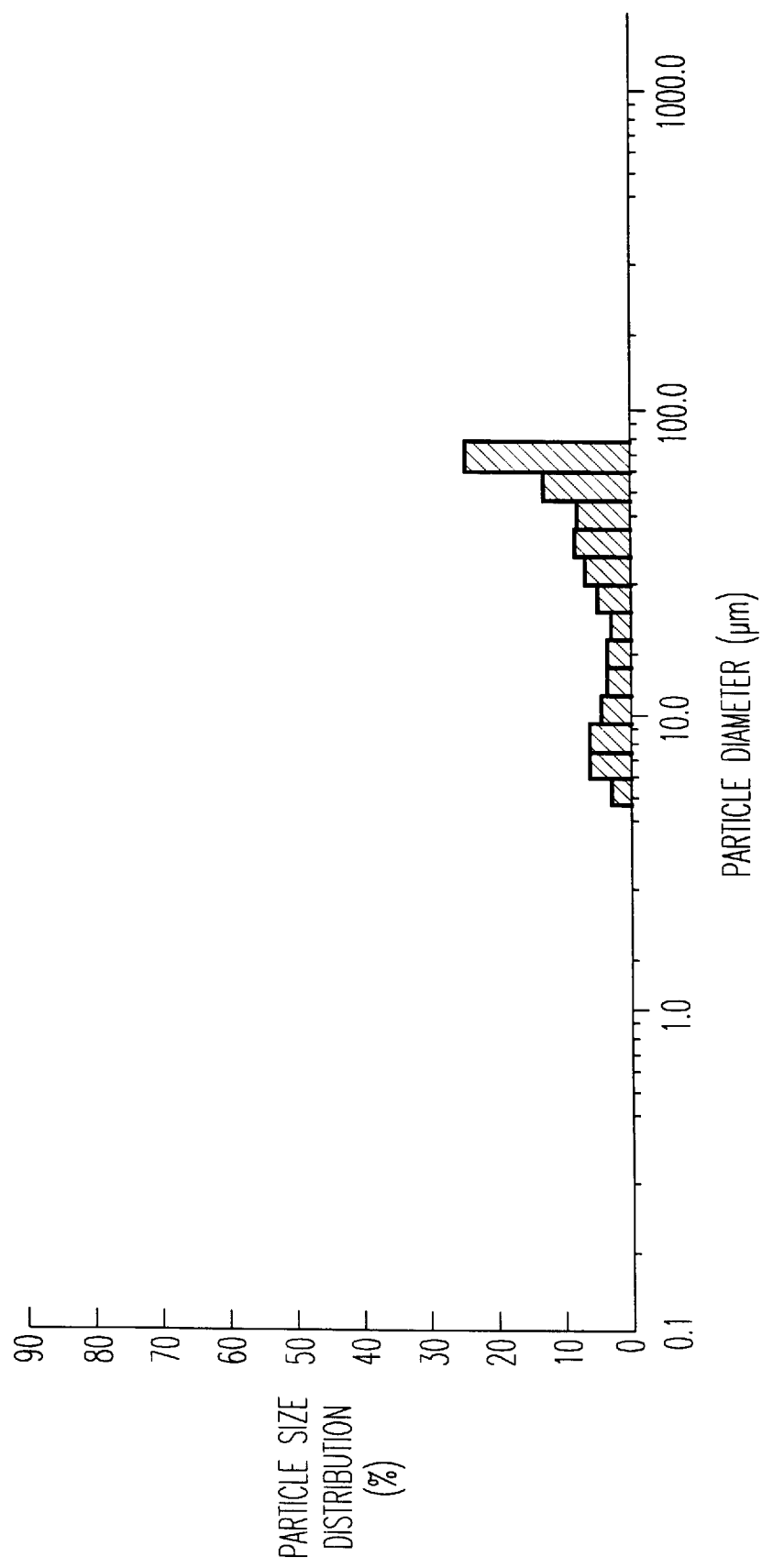
FIG. 12 represents the particle size analysis diagram of the silica used as a raw material in Example 15.
Figure 13:
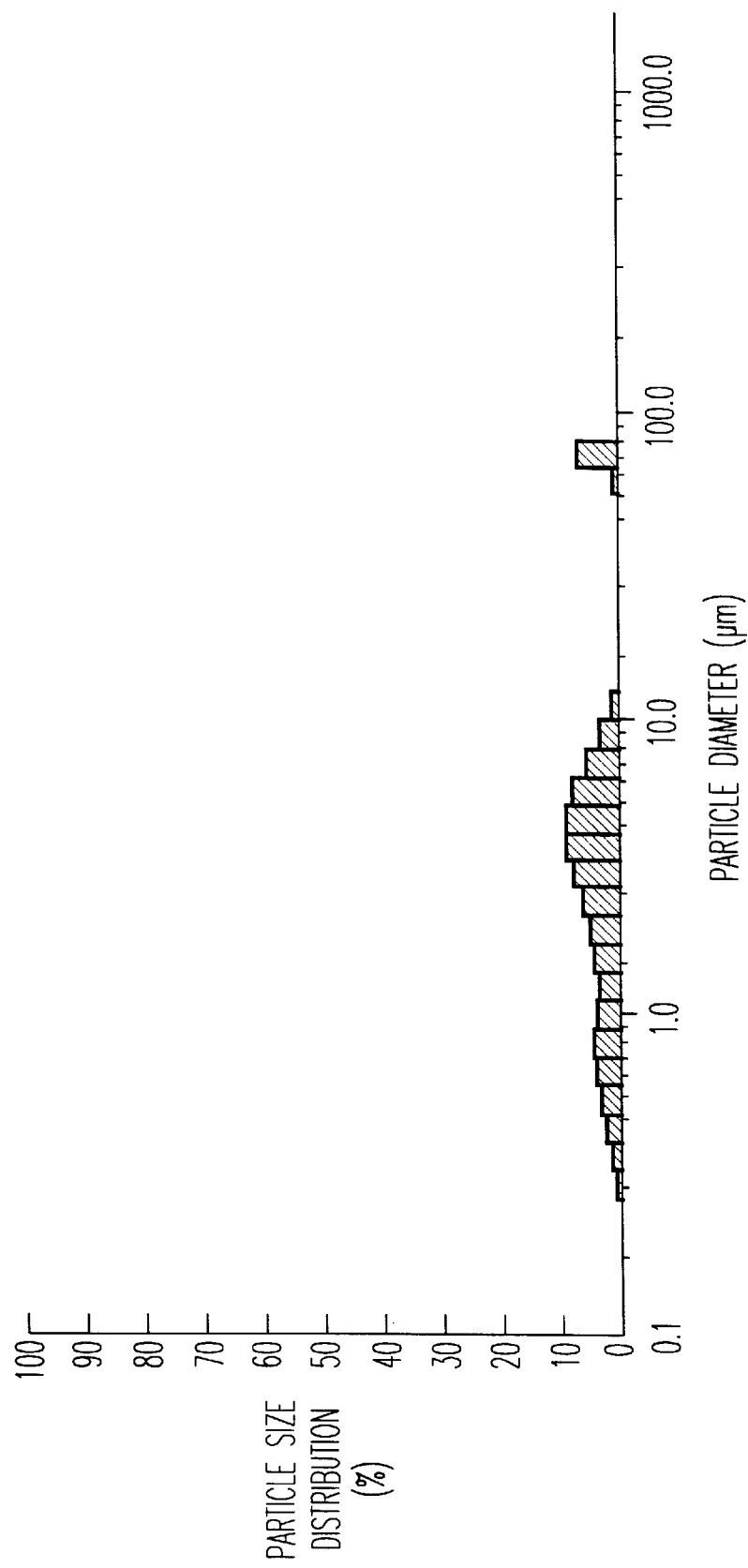
FIG. 13 represents the particle size analysis diagram of the siloxylated silica obtained in Example 15.

Silica was ground and passed through 250 mesh (which is equal to 63 μm, average particle diameter 74.33 μm, diameter range 5~80 μm, see FIG. 12). 100 g (1.66 mole) of the silica thus obtained was introduced into a 2 l polyethylene flask and then 300 ml of isopropanol and 200 ml of methanol were added thereto. 100 g (2.5 mole) of sodium hydroxide was dissolved in said silica mixture carefully in order not to raise the temperature while being stirred. The mixture was cooled down to 0~5° C. and sonicated three times, each of which for 20 minutes, under conditions of 20 kHz and 1 kW. The reaction solution sonicated was combined with the filtrate obtained after filtration of the decomposition product in Example 4 and then the resulting mixture was refluxed for 30 minutes and one hour in a water bath of 50~60° C. and 60° C. or more, respectively, while being stirred thoroughly. The reaction solution was cooled down to room temperature and centrifuged for 6 minutes at 17,400×g to separate the supernatant and precipitate. The supernatant was treated according to the same procedure for treating the filtrate in Example 4 except that trimethylchlorosilane was used as a neutralizing agent to obtain 41 g (Yield 82%) of silicone oil having an average molecular weight of 270 (molecular weight range: 150~300). While, the precipitate was treated according to the same procedure as Example 1 to obtain 87 g (Yield 87%) of siloxylated silica powder having an average particle diameter of 3.24 μm (diameter range: 0.2~10.0 μm, specific surface area: 1.476 m²/gm, see FIG. 13).

It can be seen from the above Examples that the oily or solid decomposition products prepared in Examples 10 to 13 in which the latter cleavage process was performed, have a lower average molecular weight or particle diameter than those of the decomposition products in Examples 1 to 9 in which the latter cleavage process was not performed. That is, the silicone oil prepared in Example 10 has a molecular weight of 150~300, but on the other hand the silicone oils in Examples 1 to 9 and 13 have a molecular weight of 350 to 500. Also, the silica powders prepared in Examples 11 to 13 have an average particle diameter of 0.38~0.77 μm which is much less than 86.98~87.59 μm, an average particle diameter of the silica powders prepared in Examples 1 to 9. Accordingly, it is understood that the sonication and treatment with a terminator have a conspicuous effect on raising the decomposition degree.

In addition, as can be seen from the results of Examples 14 and 15, siloxylated silica having a minute particle diameter can be obtained efficiently though the cleavage process according to the present invention is applied to silica only.

Hereinafter, the existing processes wherein primary alcohol is used as a decomposition facilitator instead of secondary and/or tertiary aliphatic alcohol are represented as Comparative Examples for the purpose of comparison.

Comparative Example 1

The same procedure as Example 1 was carried out except that 300 ml of methanol only was used instead of isopropanol to obtain 30 g (Yield 60%) of silicone oil having an average molecular weight of 480 (molecular weight range: 470~500) and 62 g of silica powder having an average particle diameter of 130 μm (diameter range: 110~170 μm).

Comparative Example 2

The same procedure as Example 1 was carried out except that 200 ml of ethanol only was used instead of isopropanol to obtain 32 g (Yield 64%) of silicone oil having an average molecular weight of 510 (molecular weight range: 500~520) and 60 g of silica powder having an average particle diameter of 150 μm (diameter range: 115~185 μm).

Comparative Example 3

The same procedure as Example 1 was carried out except that 300 ml of methanol only was used instead of isopropanol, 40 g (1 mole) of sodium hydroxide was used and the cleavage reaction was carried out for 18 hours at 50~60° C. under atmospheric pressure to obtain 37 g (Yield 74%) of silicone oil having an average molecular weight of 420 (molecular weight range: 400~450) and 55 g of silica powder having an average particle diameter of 150 μm (diameter range: 116~180.2 μm).

Comparative Example 4

The same procedure as Example 1 was carried out except that 300 ml of ethanol only was used instead of isopropanol, 40 g (1 mole) of sodium hydroxide was used and the cleavage reaction was carried out for 18 hours under conditions of room temperature and atmospheric pressure to obtain 36 g (Yield 72%) of silicone oil having an average molecular weight of 430 (molecular weight range: 400~450) and 55 g of silica powder having an average particle diameter of 150 μm (diameter range: 111~179 μm).

In the above Comparative Examples 1 to 4, alkali metal hydroxide is used as a decomposer and primary aliphatic alcohol is used as a decomposition facilitator. Accordingly, even if the amount of decomposer or decomposition facilitator is increased in the comparative examples, the results are inferior to that of the present invention which uses secondary and/or tertiary aliphatic alcohols as a decomposition facilitator. That is, the comparative examples represent yield of 60 to 74% which are much less than the yield of 90% or more according to the present invention. Furthermore, when the particle diameter of the decomposed silica is considered, the average particle diameter of silica prepared in Examples 1 to 9 (not sonicated) and Examples 11 to 13 (sonicated) have decreased by about half and by about 1/140 to 1/500, respectively, with respect to that of silica prepared in comparative examples.

According to the cleavage process of the present invention, the siloxane bond-containing compound can be efficiently decomposed to silicone oil having a low molecular weight and siloxyated silica powder having a minute particle diameter in a high yield. Particularly, if the latter cleavage process wherein the decomposition product prepared in the former cleavage process is sonicated and treated by triorganohalosilane in a nonpolar solvent is carried out, siloxylated silica powder having an average particle diameter of less than 1 μm can be prepared.

The present invention provides an effective method to convert the discarded silicone resin or rubber into a useful material. Therefore, the present invention is expected to be used advantageously in the industrial field and to have a great value for preventing environmental contamination.

What is claimed is:

1. A process for decomposing siloxane bond-containing compound by an alkali decomposer characterized in that one or more selected from a group consisting of secondary and tertiary aliphatic alcohols having 1 to 10 carbon atoms are used as a decomposition facilitator.

2. The process of claim 1, wherein the secondary aliphatic alcohol is used in an amount of 1 to 10 times by volume with respect to the tertiary aliphatic alcohol when a mixture of secondary and tertiary aliphatic alcohols is used.

3. The process of claim 1, wherein the secondary or tertiary aliphatic alcohol is selected from a group consisting of isopropanol, 2-butanol, 2-methyl-2-propanol, 2-pentanol, 3-pentanol, 2-methyl-2-butanol and t-amyl alcohol.

4. The process of claim 1, wherein primary aliphatic alcohol having 1 to 10 carbon atoms is further used in an amount of 0.1 to 1 times by volume with respect to the total amount of secondary and tertiary aliphatic alcohols.

5. The process of claim 4, wherein the primary aliphatic alcohol is one or more selected from a group consisting of methanol, ethanol, n-propanol, 1-butanol and neopentyl alcohol.

6. The process of claim 1 or 4, wherein the aliphatic alcohols are used in an amount of 30 to 300% by weight with respect to the material to be decomposed when the siloxane bond-containing compound is polyorganosiloxane compound, and the aliphatic alcohols are used in an amount of 300 to 600% by weight with respect to the material to be decomposed when the siloxane bond-containing compound is silica.

7. The process of claim 1 or 4, wherein $C_6$–$C_{10}$ alkyl is further used in an amount of 1 to 70% by weight with respect to the total amount of secondary and tertiary aliphatic alcohols.

8. The process of claim 7, wherein the alkyl is one or more selected from a group consisting of n-hexane, n-heptane, 2-methyl hexane, 3-methyl hexane, 2,3-dimethyl hexane, 2,4-dimethyl hexane, n-octane and their structural isomers.

9. The process of claim 1, wherein the decomposition product obtained after cleavage reaction is filtered, neutralized, distilled under reduced pressure and heated for 30 minutes to 4 hours at 120 to 170° C. to obtain a cyclic silicone oil in which the terminal hydroxy group is absent and only the siloxane bond is contained.

10. A process for decomposing siloxane bond-containing compound characterized in that the siloxane bond-containing compound is decomposed according to the process defined in claim 1, an alkali decomposer and one or more selected from a group consisting of secondary and tertiary aliphatic alcohols having 1 to 10 carbon atoms are introduced into the reaction system, and then the decomposition product is sonicated and treated with a triorganylhalosilane represented by the following formula [IV] in an anhydrous nonpolar solvent,

in which $R_1$, $R_2$ and $R_3$ independently of one another represent $C_1$–$C_6$ alkyl, or phenyl or vinyl which is optionally substituted, and X represents halogen.

11. The process of claim 10, wherein the sonication is carried out under conditions of 16 to 30 kHz and 0.5 to 2 kW at temperatures ranging from 0 to 5° C.

12. The process of claim 10, wherein the triorganylhalosilane is one or more selected from a group consisting of trialkylhalosilane, dialkylmonophenylhalosilane, dialkylmonovinylhalosilane, monoalkyldiphenylhalosilane, monoalkyldivinylhalosilane, triphenylhalosilane, diphenylmonovinylhalosilane, monophenyldivinylhalosilane and alkylphenylvinylhalosilane.

13. The process of claim 12, wherein the triorganylhalosilane is one or more selected from a group consisting of trimethylchlorosilane, triethylchlorosilane, triphenylchlorosilane, dimethylethylchlorosilane, diethylmethylchlorosilane, methylvinylphenylchlorosilane, ethylvinylchlorosilane, divinylmethylchlorosilane, divinylethylchlorosilane and divinylphenylchlorosilane.

14. The process of claim 10, wherein the treatment with a triorganylhalosilane is carried out in the presence of an inorganic acid.

15. The process of claim 14, wherein the inorganic acid is one or more selected from a group consisting of hydrochloric acid, nitric acid and sulfuric acid.

16. The process of claim 14, wherein the inorganic acid is used in an amount of 1 to 10 times by volume with respect to the triorganylhalosilane.

17. The process of claim 10, wherein the decomposition product is further washed with distilled water, filtered and centrifuged to obtain a solid residue, which is then dried under reduced or atmospheric pressure at temperatures ranging from 100 to 110° C.

* * * * *